United States Patent [19]
Chuang et al.

[11] Patent Number: 4,831,097
[45] Date of Patent: May 16, 1989

[54] HETEROCYCLIC CONTAINING CELLULOSIC GRAFT POLYMERS

[75] Inventors: Jui-Chang Chuang, Wayne; Ian W. Cottrell, Kinnelon; Stephen C. Johnson, Newton, all of N.J.

[73] Assignee: GAF Corporation, Wayne, N.J.

[21] Appl. No.: 169,716

[22] Filed: Mar. 21, 1988

[51] Int. Cl.$^4$ .................. C08G 89/00; A61K 7/06; A61K 7/09
[52] U.S. Cl. .................. 527/312; 527/315; 424/70; 424/71; 424/DIG. 2; 514/57; 514/846; 252/110
[58] Field of Search ............... 527/300, 312, 313, 315; 514/57, 846; 424/70, 71, DIG. 2; 252/110

[56] References Cited

U.S. PATENT DOCUMENTS 3,472,840 10/1969 Stone et al. ..................... 536/31
4,376,852  3/1983 Lindenfors ..................... 527/312
4,663,159  5/1987 Brode, II et al. ................ 536/43

Primary Examiner—John Kight
Assistant Examiner—Nathan M. Nutter
Attorney, Agent, or Firm—Marilyn J. Maue; Joshua J. Ward

[57] ABSTRACT

This invention relates to water soluble heterocyclic cationic graft polymers of cellulose containing units of the structure

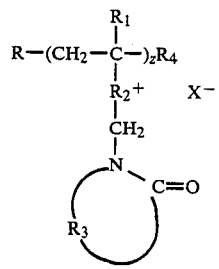

wherein R is the residue of a cellulosic polymer containing hydroxyl groups; $R_1$ is hydrogen or methyl; $R_2^+$ is a quaternized amino amide, a quaternized amino ester or a quaternized 5 or 6 membered heterocyclic ring having up to 2 nitrogen atoms in the ring structure; $R_3$ is a $C_3$ to $C_8$ alkylene group which is optionally substituted with methyl; $R_4$ is hydrogen or hydroxy; x is an integer having a value of from 1 to 1000 and X is a halide anion.

25 Claims, No Drawings

HETEROCYCLIC CONTAINING CELLULOSIC GRAFT POLYMERS

In one aspect the invention relates to novel cellulosic graft polymers and methods for their preparation. In another aspect the invention relates to the use of said polymers in skin and hair treating formulations and as antistatic agents.

BACKGROUND OF THE INVENTION

Quaternized nitrogen-containing cellulose ether derivatives are well known and possess certain desirable properties as described in U.S. Pat. No. 3,472,840, including substantivity to many substrates. However, these quaternized compounds are strongly polar and lack lipophilic groups. Thus they are of limited use in applications and systems which are relatively incompatible with polar anionic polymers and surfactants.

The high charge density of the N,N-dialkenyl-N,N-dialkyl ammonium halide cellulosic graft polymers disclosed in U.S. Pat. No. 4,464,523 and the hydrophobe substituted, quaternary nitrogen-containing cellulose ether derivatives of U.S. Pat. No. 4,663,159 employed in hair care are not easily removed by shampoos and tend to build up on the hair filaments to give a dull waxy appearance. On the other hand, the non-ionic cellulose ethers of U.S. Pat. No. 4,228,277 possess little substantivity in that they do not interact with ionic substrates such as the keratinous material of hair and skin.

Accordingly it is an object of this invention to overcome the above deficiencies and to provide a substantive, mildly cationic cellulosic graft polymer particularly suitable for conditioning and cleansing of hair and skin and useful in all applications in which quaternary nitrogen-containing cellulosic materials have been utilized.

These and other objects of the invention will become apparent from the following description and disclosure.

THE INVENTION

In accordance with this invention there is provided certain quaternized cellulosic graft polymers containing units of the structure

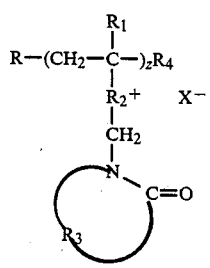 A.

wherein R is the residue of a hydroxy-containing cellulosic polymer; $R_1$ is hydrogen or methyl; $R_2^+$ is a quaternized amino amide, a quaternized amino ester or a quaternized 5 or 6 membered heterocyclic ring having from 1 to 2 nitrogen atoms in the ring structure which ring is optionally substituted with lower alkyl groups; $R_3$ is a $C_3$ to $C_8$ alkylene group which is optionally substituted with lower alkyl; $R_4$ is hydrogen or hydroxy; x is an integer having a value of from 1 to 1000 and X is a halide anion, eg. $Cl^-$, $Br^-$ or $I^-$.

The cellulosic residue is derived from cellulose compounds including $C_1$ to $C_4$ alkylated cellulose, hydroxy $C_2$ to $C_3$ alkyl cellulose, carboxy $C_1$ to $C_2$ alkyl cellulose, hydroxy $C_2$ to $C_3$ alkyl methyl cellulose and hydroxyethyl carboxymethyl cellulose. These cellulosic polymers are water soluble and contain 50 to 20,000 anhydroglucose units. Preferred of this group are cellulose derivatives having the structure:

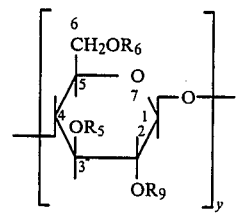

wherein y has a value of from 50 to 20,000, preferably from 200 to 8,000, and $R_5$, $R_6$ and $R_9$ are each hydrogen, hydroxy, lower alkyl, lower hydroxyalkyl, lower alkoxyalkyl, carbhoxymethyl or carboxymethyl lower hydroxyalkyl. Although grafting of the quaternized monomer onto the cellulose polymers can take place at any one or more of the hydroxy groups at 2, 3 and 6 positions of the anhydroglucose unit, it is preferred that not more than one graft per anhydroglucose unit be present in the product and while grafting along the anhydroglucose backbone can be randomly distributed among positions 2, 3 and 6, most often the comonomeric moiety attaches to the 6th position. Generally, in the polymers of the present invention, between about 1% and about 50%, more desirably between about 2% and about 25%, of the cellulosic units contain a grafted moiety. When the product is to be employed for hair treatment, it is recommended that the cellulosic polymer contains less than 20% by weight of a quaternized monomer, thus assuring lack of polymer build up on hair. For other uses such as skin conditioning, flocculation, anti-static uses, up to about 50% of a quaternized monomer can be present in the cellulosic polymer.

The cationic, quaternized comonomers for grafting onto the cellulosic polymers of the present invention are those described by the formula

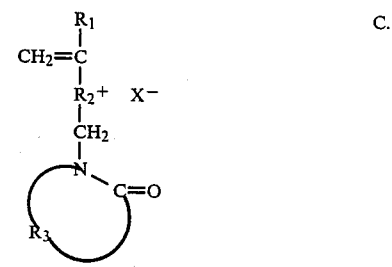 C.

wherein $R_1$, $R_2$ and $R_3$ are as defined above and wherein $R_2^+$ is an N-quaternized moiety having from 4 to 29 carbon atoms. The product of the invention can contain from 1 to 1000, preferably from 5 to 200 of such quaternary units. Preferred cationic, quaternized comonomers within this group are the N-methylpyrrolidonyl chloride salts of the above formula C wherein $R_2^+$ is

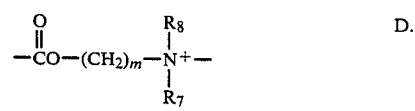 D.

-continued

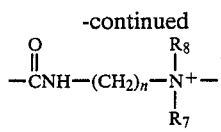

E.

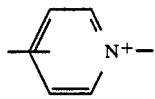

F.

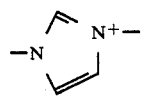

G.

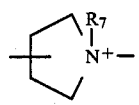

H.

and wherein X is a chloride ion; $R_3$ is —$(CH_2)_3$—; m and n each have a value of from 1 to 20 and $R_7$ and $R_8$ are each lower alkyl, most preferably methyl. Suitable graft comonomers of the preferred type include the addition products of N-chloromethyl-2-pyrrolidone and N,N-dimethylaminomethyl acrylate, N,N-dimethylaminoethyl methacrylate, N-vinylimidazole, 2-vinylpyridine, 4-vinylpyridine, N,N-dimethylaminopropyl methacrylate, N,N-diethylaminoethyl acrylate, N,N-dimethylaminoethyl acrylamide, N,N-diethylaminoethyl methacrylamide and the like.

The quaternized graft cellulosic copolymers of this invention exhibit excellent thickening power in aqueous solutions thus eliminating the need for extraneous thickeners. The compounds have also been found to have superior hair and skin substantivity and conditioning properties. On the skin, the present copolymers provide a moisturizing effect. When formulated into a shampoo or hair conditioner, the compositions leave the hair soft and silky with excellent wet combability. These grafted copolymers can be applied to the skin or hair in conventional formulations such as commercial shampoos, permanent waving solutions, hair styling gels and mousses, fixing agents in hair dyes, finishing rinses, skin rejuvenating and moisturizing formulations, etc. or they can be applied directly in aqueous solutions. The present copolymers can also be employed as dye fixing agents in processing formulations for dying of furs or leather.

The concentration of the present polymers in a formulation or aqueous solution can vary from about 0.01% to about 10%, preferably from about 0.2% to about 3%, of the total composition. The excellent rinsability and the mildly cationic character of the present polymers is provided by the presence of N-heterocyclic lactam moieties on the cellulosic polymers. Since the average of quaternized sites in the cellulosic copolymeric product is preferably less than one per anhydroglucose unit, as opposed to frequent or multiple cationization of the anhydroglycose units, these polymers are not strongly cationic. Generally the polymer products have a pH of between about 5.5 and 8, more usually between 5.8 and 6.8, which is ideally suited to render hair at pH 4, more neutral. The presence of the heterocyclic lactam groups also promote substantivity.

In general, the cationic comonomers of this invention are defined by the formula

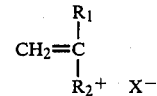

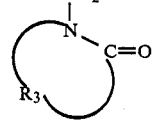

These quaternized amino lactams are prepared by reacting a N-chloromethyl-, N-bromomethyl- or N-iodomethyl-heterocyclic lactam having 4 to 9 carbon atoms in the ring with a vinyl compound, an acrylate or methacrylate, an acrylamide or methacrylamide each having terminal tertiary amino groups, or a vinyl substituted 5 or 6 membered N-heterocyclic ring compound having up to 2 nitrogen atoms in the ring structure which is optionally substituted with lower alkyl groups. The reaction is effected using about stochiometric amounts of reactants in an inert solvent such as toluene, acetone, xylene, cyclohexane, benzene, wherein the concentration of reactants is between about 20% and about 50%. The mixture is reacted at a temperature of between about 0° C. and about 50° C. for a period of from about 0.5 to about 10 hours. After the reaction is completed, the solvent is removed by filtration, decantation or evaporation and the resulting solid quaternized product is rinsed with solvent, vacuum dried and recovered in quantitative yield.

The unsaturated quaternized heterocyclic monomer, preferably the unsaturated quaternized salt of N-chloromethyl-2-pyrrolidone, can be directly contacted with the cellulosic polymer or it can be polymerized to a mixture of oligomers, and the polymerized intermediate grafted onto the cellulosic chain. Alternatively, when it is desired to produce a graft polymer having high molecular weight polymeric side chains, the cellulosic polymer can be contacted with a large excess of the monomeric comonomer. In this case, some polymerization of the unsaturated quaternized heterocyclic monomer takes place in situ simultaneous with the grafting onto the cellulosic backbone. In most reactions a mole ratio of anhydroglucose units in the cellulose polymer to quaternized monomer of between about 30:1 and about 3:1, preferably between about 20:1 and about 4:1, is employed.

In the process for synthesizing the graft copolymer of this invention, the cellulosic polymer and the quaternized monomer are swelled in a suitable solvent, conveniently an aqueous solution of an inert, water-miscible solvent such as for example acetone, isopropanol, methyl ethyl ketone, etc., and is stirred for a period of from about 0.5 to about 8 hours. A free radical peroxide initiator in aqueous solution is then stirred into the solution. A ferrous salt activator is also added and reaction ensues. A second portion of the peroxide may also be added if desired. The mixture is reacted over a period of from about 2 to about 10 hours at a temperature within the range of from about 0° C. to about 80° C., preferably between about 20° C. and about 30° C. The reaction product is then separated from the supernate by filtration and is washed with a suitable liquid, such as for example, acetone, isopropanol, methyl ethyl ketone, etc. and, if necessary, the pH is adjusted to between about 5.5 and about 8 with a conventional base; although usually no adjustment is necessary since the products normally have a pH of 5.8 to 6.8. The product is recovered by filtration or any other convenient means and dried. Suitable free radical redox initiators for the above reaction include a peroxide such as hydrogen peroxide, t-butyl hydroperoxide, employed with a ferrous salt activator such as ferrous citrate, ferrous chloride, ferrous gluconate, ferrous nitrate, ferrous sulfate heptahydrate, ferrous ammonium sulfate hexahydrate, ferrous ethylene diaminetetraacetic acid complex, etc. These ferrous salts are employed with peroxide in a concentration of between about 0.01 and about 0.2 mole % based on peroxide. A ceric ammonium nitrate in one normal nitric acid may also be employed as the initiator in place of the free radical redox initiators.

The above process results in the production of a cellulose copolymer wherein the hydrogen atom of a hydroxy group of the hydroxylated cellulose is replaced with the quaternized amino lactam group. More specifically, the products of the invention are cellulosic graft polymers containing units

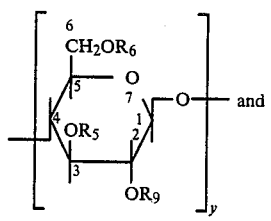

(a)

(b) units of (1) wherein at least one hydrogen of $R_5$, $R_6$ and $R_9$ is replaced by a quaternized amino lactam having the structure

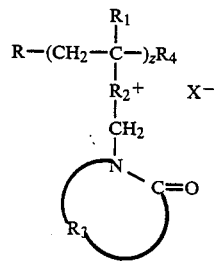

wherein $R_1$ is hydrogen or methyl; $R_2$ is a quaternized $C_4$ to $C_{29}$ moiety of an amino amide, an amino ester or a cyclic amine having 1 to 2 nitrogen atoms in a 5 to 6 membered N-heterocyclic ring, which ring is optionally substituted with lower alkyl; $R_3$ is $C_3$ to $C_8$alkylene optionally substituted with lower alkyl; $R_4$ is hydrogen or hydroxy; $R_5$, $R_6$ and $R_9$ are each hydrogen, hydroxy, lower alkyl, lower hydroxyalkyl, lower alkyloxy alkyl, carboxymethyl or carboxymethyl lower hydroxy alkyl; X is a halide anion and z is an integer having a value of from 1 to 1000.

Generally the product contains from about 50 mole % to about 99 mole % of component (a), preferably from about 75 mole % to about 98 mole % of component (a) and most preferably the graft product wherein only one of $R_5$, $R_6$ and $R_9$ in component (b) is substituted with a quaternized amino lactam.

Having thus generally described the invention, reference is now made to the following examples which are illustrative of preferred embodiments but which are not to be construed as limiting to the scope of the invention as more broadly set forth above and in the appended claims. All parts given are by weight unless otherwise indicated.

EXAMPLE 1

Preparation of Cationic Comonomers

Novel cationic comonomers were prepared by reacting N-chloromethylpyrrolidone (CMP) with a monomer containing a tertiary amine in a molar ratio of 1:1 in dry toluene solvent at 0°–5° C. The weight ratio of reactants to diluent solvent was kept at 1:3. For the ease of handling, CMP was diluted with 20% of the total volume of toluene before charging. Thus, into a 4-necked, one-liter resin kettle fitted with an anchor agitator (200 rpm), a dropping funnel, a drying tube and a thermometer, 66.80 g. of CMP (0.50 mole) in 82.0 g. of toluene was charged dropwise into 78.60 g. N,N-dimethylaminoethyl methacrylate (DMAEMA, 0.50 mole) in 350.0 g. of toluene at 0°-5 C. over a 60 minute period to form the corresponding quaternary ammonium salt, 2-methacryloxyloxyethyl[(1-pyrrolidonyl)methyl]-dimethyl ammonium chloride (MEPDAC). Upon the completion of charging, mixing was continued for an additional six hours. The precipitated MEPDAC monomer was separated from toluene, washed with dry acetone and vacuum dried in a 45° C. oven and the product was recovered in quantitative yield.

The identical procedure was used to react CMP with each of N-vinylimidazole, 4-vinylpyridine and N,N-dimethylaminopropyl methacrylamide (DMAPMA) to yield 3-[(1-pyrrolidonyl)methyl]-1-vinylimidazolium chloride (PMVIC),1-[(1-pyrrolidonyl)methyl]-4-vinylpyridinium chloride (PMVPC), and 3-methacrylamidopropyl [(1-pyrrolidonyl)methyl]dimethyl ammonium chloride (MAPPDAC), respectively. These products were obtained in quantitative yield. The structures of all four of these cationic monomers were determined by FT-IR and NMR. Their carbon content, nitrogen content and melting points are summarized as follows:

|         | %N* | | %C.* | | |
|---------|------|-------|-------|-------|----------|
|         | Calc. | Found | Calc. | Found | M.P.,° C. |
| MEPDAC  | 9.63  | 9.66  | 53.69 | 53.57 | 170–172  |
| MAPPDAC | 13.83 | 13.49 | 55.35 | 55.30 | 147      |
| PMVIC   | 18.45 | 18.39 | 52.75 | 52.14 | 188–189  |
| PMVPC   | 11.74 | 11.53 | 60.38 | 59.77 | 134–135  |

*Determined by an elemental analyzer.

The identical procedure employed above is also used to react CMP with 1-vinyl-2-methylimidazole, 2-vinylpyridine and N-methyl-n<N-diallylamine to produce 3-[(1-pyrrolidonyl)methyl]-2-methyl-1-vinylimidazolium chloride, 1-[(1-pyrrolidonyl)methyl]2-vinylpyridinium chloride and [(1-pyrrolidonyl)methyl]diallylmethyl ammonium chloride, respectively, in quantitative yield.

EXAMPLE 2

This Example illustrates the preparation of the MEPDAC-hydroxyethyl cellulose graft copolymer by ferrous ion/hydrogen peroxide redox initiation in an acetone/water mixture.

Into a 4-necked, 1-liter resin kettle fitted with an anchor agitator, a nitrogen inlet tube, a condenser and a thermometer, charge 114.72 g. of hydroxyethyl cellulose (HEC, Natrosol ® 250KR from Hercules, 5% moisture content), 11.64 g. of methacryloyloxyethyl[(1-pyrrolidonyl)methyl]dimethyl ammonium chloride (MEPDAC), 395.0 g. of acetone/distilled water (85/15) mixture, and the mixture was stirred (200 rpm) under nitrogen bubbling (50 ml/min.) at 25° C. for 7 hours. Then 0.4448 g. of ferrous sulfate ($FeSO_4 \cdot 7H_2O$) in 5.0 ml of disstilled water was added. After five minutes, 1.8132 g. of 30% hydrogen peroxide was added dropwise. After 60 more minutes, 0.9066 g. of 30% hydrogen peroxide was added dropwise. The reaction mixture was then stirred under nitrogen bubbling for 3 hours. The reaction product was de-watered by adding 200 g. of acetone and allowed to stand overnight.

The reaction product was then separated from the reaction medium by filtration, tray dried overnight in a 45° C. oven and finally vacuum dried to constant weight at room temperature. It was recovered in the form of beige, free-flowing powder after grinding and screening through a 40-mesh sieve. The yield was 93.6%.

The MEPDAC-HEC graft copolymer thus obtained, referred to as Polymer 1, has a nitrogen content of 0.75% by Kjeldahl method which corresponds to the presence of 7.8% MEPDAC monomer grafted onto the cationic cellulose polymer. A 2% solution of this product in water is clear and has a pH of 6.4 and a Brookfield viscosity of 1600 cps at 25° C.

EXAMPLE 3

This example illustrates the preparation of MEPDAC-hydroxyethyl cellulose graft copolymer by ferrous ion/hydrogen peroxide redox initiation in an isopropanol/water mixture.

In this example the apparatus identical to that described in Example 2 was used. A mixture of 27.20 g. of hydroxyethyl cellulose (HEC), 7.27 g. of MEPDAC monomer, and 100.0 g. of isopropanol/water (88/12) mixture was stirred (200 rpm) under nitrogen bubbling (50 ml/min.) at 25° C. for 7 hours. Then 0.1112 g. of ferrous sulfate ($FeSO_4 \cdot 7H_2O$) in 2.0 ml of distilled water was added. After 5 minutes, 0.4533 g. of 30% hydrogen peroxide was added dropwise. After one hour, 0.1133 g. of 30% hydrogen peroxide was added dropwise. The reaction mixture was then stirred under nitrogen bubbling (50 ml/min.) for 6 hours. The reaction product was de-watered by adding 50.0 g. of acetone and allowed to stand overnight.

The reaction product was then separated from the reaction medium by filtration, tray dried overnight in a 45° C. oven and finally vacuum dried to constant weight at room temperature. It was recovered in the form of beige, free-flowing powder after grinding and screening through a 40-mesh sieve. The yield was 95.7%.

The MEPDAC-HEC graft copolymer thus obtained, referred to as Polymer 2, has a nitrogen content of 1.23% by Kjeldahl method which corresponds to the presence of 12.8% MEPDAC monomer grafted onto the cationic cellulose polymer. A 2% solution of this product in water is clear and has a pH of 6.8 and a Brookfield viscosity of 1440 cps at 25° C.

EXAMPLE 4

This example illustrates the preparation of the MEPDAC-hydroxyethyl cellulose graft copolymer at a higher cationic monomer level by ferrous ion/hydrogen peroxide redox initiation in an acetone/water mixture.

In this example the apparatus identical to that described in Example 2 was used. A mixture of 28.68 g. of hydroxyethyl cellulose (HEC)

5.82 g. of MEPDAC monomer, and 100.0 g. of acetone/water (85/15) mixture was stirred (200 rpm) under nitrogen bubbling (50 ml/min.) for 6 hours. Then 0.1112 g. of ferrous sulfate ($FeSO_4 \cdot 7H_2O$) in 2.0 ml of distilled water was added. After 5 minutes, 0.4533 g. of 30% hydrogen peroxide was added dropwise.

After one hour, 0.1133 g. of 30% hydrogen peroxide was added dropwise. The reaction mixture was then stirred under nitrogen bubbling for an additional 3 hours. The reaction product was de-watered by adding 50.0 g. of acetone and allowed to stand overnight.

The reaction product was then separated from the reaction medium by filtration, tray dried overnight in a 45° C. oven and finally vacuum dried to constant weight at room temperature. It was recovered in the form of beige, free-flowing powder after grinding and screening through a 40-mesh sieve. The yield was 93.9%.

The MEPDAC-HEC graft copolymer thus obtained, referred to as Polymer 3, has a nitrogen content of 1.12% by Kjeldahl method which corresponds to the presence of 11.6% MEPDAC monomer grafted onto the cationic cellulose polymer. A 2% solution of this product in water is clear and has a pH of 6.6 and a Brookfield viscosity of 1320 cps at 25° C.

EXAMPLE 5

This example illustrates the preparation of the PMVPC-hydroxyethyl cellulose graft copolymer by ferrous ion/hydrogen peroxide redox initiation in an acetone/water mixture.

In this example the apparatus identical to that described in Example 2 was used. A mixture of 57.36 g. of hydroxyethyl cellulose (HEC)

4.78 g. of PMVPC monomer, and 200.0 g. of acetone/water (85/15) mixture was stirred (200 rpm) under nitrogen bubbling (50 ml/min.) at 25° C. for 6 hours. Then 0.9066 g. of 30% hydrogen peroxide was added dropwise. After 5 minutes, 0.3136 g. of ferrous ammonium sulfate [$Fe(NH_4)_2(SO_4)_2 \cdot 6H_2O$] in 4.0 ml of distilled water was added dropwise. After 5 more minutes, 0.4533 g. of hydrogen peroxide was added dropwise. The reaction mixture was then stirred under nitrogen bubbling for an additional 6 hours. The reaction product was de-watered by adding 100.0 g. of acetone.

The reaction product was then separated from the reaction medium by filtration, tray dried overnight in a 45° C. oven and finally vacuum dried to constant weight at room temperature. It was recovered in the form of beige, free-flowing powder after grinding and screening through a 40-mesh sieve. The yield was 98.9%.

The PMVPC-HEC graft copolymer thus obtained, referred to as Polymer 4, has a nitrogen content of 0.78% by Kjeldahl method which corresponds to the presence of 8.1% PMVPC monomer grafted onto the cationic cellulose polymer. A 2% solution of this product in water is clear and has a pH of 5.2 and a Brookfield viscosity of 1360 cps at 25° C.

EXAMPLE 6

This example illustrates the preparation of MAPPDAC-hydroxyethyl cellulose graft copolymer by ferrous ion/hydrogen peroxide redox initiation in an acetone/water mixture.

In this example the apparatus and procedure identical to that described in Example 5 were used. The weight ratios of the reactants, reaction medium and redox initiators were also identical to that described in Example 5 except 4.78 g. of PMVPC monomer was replaced by 6.08 g. of MAPPDAC monomer. The reaction product was recovered in the form of beige, free-flowing powder after grinding and screening through a 40-mesh sieve, the yield was 97.7%.

The MAPPDAC-HEC graft copolymer thus obtained, referred to as Polymer 5, has a nitrogen content of 0.97% by Kjeldahl method which corresponds to the presence of 7.0% MAPPDAC monomer grafted onto the cationic cellulose polymer. A 2% solution of this product in water is clear and has a pH of 6.0 and a Brookfield Viscosity of 1360 cps at 25° C.

EXAMPLE 7

This example illustrates the preparation of MEPDAC-hydroxyethyl cellulose graft copolymer by ferrous ion/sodium metabisulfite/hydrogen peroxide redox initiation in an acetone/water mixture.

In this example the apparatus identical to that described in Example 2 was used. A mixture of 57.36 g. of hydroxyethyl cellulose (HEC),
5.82 g. of MEPDAC monomer, and
200.0 g. of acetone/water (85/15) mixture was stirred (200rpm) under nitrogen bubbling (50 ml/min.) at 25° C. for 6 hours.

After 0.4533 g. of 30% hydrogen peroxide was added dropwise, the following ingredients were added at 5 minutes intervals:

(1) 0.0111 g. of ferrous sulfate ($FeSO_4.7H_2O$) in 2.0 ml of distilled water
(2) 0.0760 g. of sodium metabisulfite ($Na_2S_2O_5$) in 2.0 ml of distilled water
(3) 0.2267 g. of 30% hydrogen peroxide.

The reaction mixture was then stirred under nitrogen bubbling for 8 hours. The reaction product was de-watered by adding 100.0 g. of acetone and allowed to stand overnight.

The reaction product was then separated from the reaction medium by filtration, tray dried overnight in a 45° C. oven and finally vacuum dried to constant weight at room temperature. It was recovered in the form of beige, free-flowing powder after grinding and screening through a 40-mesh sieve. The yield was 95.0%.

The MEPDAC-HEC graft copolymer thus obtained, referred to as Polymer 6, has a nitrogen content of 0.53% by Kjeldahl method which corresponds to the presence of 5.5% MEPDAC monomer grafted onto the cationic cellulose polymer. A 2% solution of this product in water is clear and has a pH of 6.4 and a Brookfield viscosity of 1640 cps at 25° C.

EXAMPLE 8

This example illustrates the preparation of MEPDAC-hydroxyethyl cellulose graft copolymer by $Fe(EDTA)^{2-}$*/hydrogen peroxide redox initiation in an acetone/water (85/15) mixture. *iron (II) ethylenediaminetetraacetic acid complex In this example the apparatus identical to that described in Example 2 was used. A mixture of 57.36 g. of hydroxyethyl cellulose (HEC),
5.82 g. of MEPDAC monomer, and
200.0 g. of acetone/water (85/15) mixture was stirred (200 rpm) under nitrogen bubbling (50 ml/min.) for 8 hours. Then 0.9066 g. of 30% hydrogen peroxide was added dropwise. After 5 minutes, 0.2976 g. of ethylenediaminetetracetic acid disodium salt dihydrate ($Na_2H_2EDTA.2H_2O$) in 4.0 ml of distilled water was mixed with 0.3136 g. of ferrous ammonium sulfate $[FE(NH_4)_2(SO_4)_2.6H_2O]$ and the clear solution was poured into the reaction kettle. After 5 more minutes, 0.4533 g. of 30% hydrogen peroxide was added dropwise. The reaction mixture was then stirred for an additional three hours and allowed to stand overnight.

The reaction product was de-watered by adding 100.0 g. of acetone and stirred for one hour. It was then separated from the reaction medium by filtration, tray dried overnight in a 45° C. oven and finally vacuum dried to constant weight at room temperature. The product was recovered in the form of beige, free-flowing powder after grinding and screening through a 40-mesh sieve. The yield was 95.9%.

The MEPDAC-HEC graft copolymer thus obtained, referred to as Polymer 7, has a nitrogen content of 0.82% by Kjeldahl method which corresponds to the presence of 8.5% MEPDAC monomer grafted onto the cationic cellulose polymer. A 2% solution of this product in water is clear and has a pH of 5.6 and a Brookfield viscosity of 260 cps at 25° C.

EXAMPLE 9

This example repeats the preparation of MEPDAC-hydroxyethyl cellulose graft copolymer using apparatus and procedure identical to that described in Example 8. The identical weight ratios of the reactants, reaction medium and redox initiators were employed except MEPDAC monomer was reduced from 5.82 g. to 4.65 g. The reaction product was recovered in the form of beige, free-flowing powder after grinding and screening through a 40-mesh sieve. The yield was 96.1%.

The MEPDAC-HEC graft copolymer thus obtained, referred to as Polymer 8, has a nitrogen content of 0.62% by Kjeldahl method which corresponds to the presence of 6.5% MEPDAC monomer grafted onto the cationic cellulose polymer. A 2% solution of this product in water is clear and has a pH of 5.3 and a Brookfield viscosity of 480 cps at 25° C.

EXAMPLE 10

This example illustrates the preparation of high viscosity grade of MEPDAC-hydroxyethyl cellulose graft copolymer using apparatus and procedure identical to that described in Example 8. The identical weight ratios of the reactants, reaction medium and redox initiators were employed except 57.36 g. of medium viscosity grade hydroxyethyl cellulose (Natrosol ® 250 KR, Hercules) were replaced by a high viscosity grade HEC (Natrosol ® 250 HHR) and 0.3136 g. of ferrous ammonium sulfate was replaced by 0.2224 g. of ferrous sulfate. The reaction product was recovered in the form of beige, free-flowing powder after grinding and screening through a 40-mesh sieve. The yield was 90.7%.

The MEPDAC-HEC graft copolymer thus obtained, referred to as Polymer 9, has a nitrogen content of 0.70% by Kjeldahl method which corresponds to the presence of 7.3% MEPDAC monomer grafted onto the cationic cellulose copolymer. A 2% solution of this product in water is clear and has a pH of 4.3 and a Brookfield viscosity of 5400 cps at 25° C.

EXAMPLE 11

This example illustrates the preparation of PMVIC-hydroxyethyl cellulose graft copolymer using apparatus and procedure identical to that described in Example 8. The identical weight ratios of the reactants, reaction medium and redox initiators were employed except 5.82 g. of MEPDAC monomer was replaced by 4.56 g. of PMVIC monomer. The reaction product was recovered in the form of beige, free-flowing powder after grinding and screening through a 40-mesh sieve. The yield was 95.5%.

The PMVIC-HEC graft copolymer thus obtained, referred to as Polymer 10, has a nitrogen content of 1.07% by Kjeldahl method which corresponds to the presence of 5.8% PMVIC monomer grafted onto the cationic cellulose polymer. A 2% solution of this product in water is clear and has a pH of 5.5 and a Brookfield viscosity of 580 cps at 25° C.

EXAMPLE 12

This example illustrates the preparation of PMVIC-hydroxyethyl cellulose graft copolymer by ceric ion initiation.

Into a 4-necked, 1-liter resin kettle fitted with an anchor agitator, a nitrogen inlet tube, a condenser and a thermometer, charge
- 57.36 g. of hydroxyethyl cellulose (HEC, Natrosol 250 KR from Hercules, 5% moisture content),
- 9.11 g. of 3-[(1-pyrrolidonyl)methyl]-1-vinylimidazolium chloride (PMVIC), and
- 200.0 g. of acetone/water (85/15) mixture.

The mixture was stirred (200 rpm) under nitrogen bubbling (50 ml/min.) at 25° C. for 7 hours. Then 20.0 ml of freshly prepared ceric ammonium nitrate solution (0.1 N in 1 N nitric acid) were added dropwise. The yellow color of ceric ion faded within 5 minutes. The reaction mixture was stirred for 8 hours and allowed to stand overnight. After decanting the reaction medium, the reaction product was washed with 200 g. of acetone, neutralized to pH 6.5 with 14% ammonium hydroxide, and separated by filtration. The reaction product was tray dried overnight in a 45° C. oven and then vacuum dried to constant weight at room temperature. It was recovered in the form of beige, free-flowing powder after grinding and screening through a 40-mesh sieve. The yield was 89.4%.

The PMVIC-HEC graft copolymer thus obtained, referred to as Polymer 11, has a nitrogen content of 1.73% by Kjeldahl method which corresponds to the presence of 9.4% PMVIC monomer grafted onto the cationic cellulose polymer. A 2% solution of this product in water is clear and has a pH of 4.3 and a Brookfield viscosity of 1240 cps at 25° C.

EXAMPLE 13

This example illustrates the preparation of MEPDAC-hydroxyethyl cellulose graft copolymer by ceric ion initiation using apparatus and procedure identical to that described in Example 12. The identical weight ratios of the reactants, reaction medium and ceric ion initiator were employed except 9.11 g. of PMVIC monomer was replaced by 5.82 g. of MEPDAC monomer. The reaction product was recovered in the form of beige, free-flowing powder after grinding and screening through a 40-mesh sieve. The yield was 98.2%.

The MEPDAC-HEC graft copolymer thus obtained, referred to as Polymer 12, has a nitrogen content of 0.80% by Kjeldahl method which corresponds to the presence of 8.3% MEPDAC monomer grafted onto the cationic cellulose polymer. A 2% solution of this product in water is clear and has a Brookfield viscosity of 1160 cps at 25° C.

EXAMPLE 14

Substantivity Test

This example demonstrates the excellent substantivity to the hair of the water-soluble, heterocyclic, cationic cellulose graft polymers of this invention.

A swatch of light blonde hair (ca. 0.3 g. and 3 inches in length) was thoroughly washed with ethanol (SDA-40) and dried under a hair dryer. The hair swatch was submersed in 1% solution of the cationic cellulose graft polymer of Example 2 for one minute, rinsed in warm tap water for one minute, dried with the blotting paper, immersed in a 0.5% aqueous anionic red dye (diphenyl scarlet 4SWN, Ciba-Geigy), for one minute, rinsed thoroughly in running tap water for 2 minutes and dried under a hair dryer. The tested hair swatch had acquired a substantive red color, resulting from the interaction between the negatively charged red dye molecules and the positively charged graft copolymer deposited on the surface of the hair.

An additional 11 repeat experiments, using each of the cationic cellulose, graft polymers of Examples 3–13 in place of the cationic cellulose graft polymer of Example 2. All exhibited substantive red color on the hair swatch.

In a separate experiment, three swatches of light blonde hair (ca. 0.3 g. and 3 inches in length) were each thoroughly washed with ethanol (SDA-40) and dried under a hair dryer. The first hair swatch was subjected to the substantivity test described above using the polymer of Example 2 and exhibited a substantive red color. The second hair swatch was also submersed in the same polymer solution and rinsed with warm water but not immersed in the red dye solution. The hair swatch was then washed with Breck ® shampoo (1:1 dilution with water) and dried under a salon dryer. After four more shampooing-drying cycles, the hair swatch exhibited an extremely light pink color on the substantivity test. The same test procedure was also performed on the third hair swatch except it was subjected to ten shampooing-drying cycles. The hair swatch showed no red or pink color on the substantivity test, indicating that no polymer remained to interact with the dye and provide the red color. This is an indication that the cationic cellulose polymers of this invention can be used repeatedly to treat hair without causing a polymer build-up problem.

EXAMPLE 15

Wet Combing Test

This test demonstrates the improvement in the ease of wet combing on a hair tress that has been treated with a cationic cellulose polymer as the "conditioning" agent. A wet hair tress was combed three times and the drag force resisted to comb through was assigned to a score of 1 to 10 with "1" representing "very heavy comb drag" and "10" representing "no drag" (i.e. comb falls through). The wet comb drag of a hair tress was evaluated under the following three consecutive steps:

1. The hair tress was immersed in distilled water, squeezed through fingers and combed three times.

2. The damp hair tress was then immersed in a 1% aqueous cationic cellulose polymer for one minute, squeezed with a squeegie and combed three times.
3. The coated hair tress was immersed in a beaker of distilled water for 30 seconds by dipping up and down ten times, transferred (without squeezing) to a second beaker of distilled water for 30 seconds by dipping up and down ten times, squeezed with a squeegie and combed three times.

The Wet Comb results on hair tresses treated with the cationic cellulose graft copolymers of Examples 2–13 are reported as follows:

| Polymer of Example | Composition | Wet Comb | | |
|---|---|---|---|---|
| | | After dipping in water | After dipping cationic polymer | After Rinsing |
| 2 | MEPDAC—HEC | 4 | 10 | 10 |
| 3 | MEPDAC—HEC | 4 | 10 | 10 |
| 4 | MEPDAC—HEC | 4 | 10 | 8 |
| 5 | PMVPC—HEC | 4 | 9 | 9 |
| 6 | MAPPDAC—HEC | 4 | 7 | 9 |
| 7 | MEPDAC—HEC | 4 | 10 | 10 |
| 8 | MEPDAC—HEC | 4 | 10 | 10 |
| 9 | MEPDAC—HEC | 4 | 9 | 9 |
| 10 | MEPDAC—HEC | 4 | 9 | 9 |
| 11 | PMVIC—HEC | 3 | 8 | 6 |
| 12 | PMVIC—HEC | 4 | 10 | 10 |
| 13 | MEPDAC—HEC | 4 | 10 | 10 |

All hair tresses showed an improvement in the ease of wet combing after treating with one of the water-soluble heterocyclic cationic cellulose graft polymers of this invention (polymers of Examples 2–13), which is one of the excellent characteristics for formulating "conditioning" shampoos. The treated hair tresses exhibited excellent manageability and had no build-up or a greasy feel.

EXAMPLE 16

(Comparative)

As discussed above, it is essential in the preparation of cationic cellulose graft polymers of the present invention containing N-alkylene-2-pyrrolidone or N-alkylene caprolactam moiety to the quaternary nitrogen.

The following experiment was carried out to establish that grafting of a tertiary amine containing monomer, without quaternizing with a lactam-containing moiety, failed to provide the substantivity to hair and the improvement in wet combing.

To a one-liter resin with attachments identical to Example 2 was added 28.68 g. of hydroxyethylcellulose (Natrosol ® 250 KR, Hercules), 3.14 g. of N,N-dimethylaminoethyl methacrylate (DMAEMA, CPS Chemical Co.)

100.0 g. of acetone/water (85/15) mixture and the mixture was stirred (150 rpm) under nitrogen bubbling (50 ml/min.) for 7 hours. Then 0.1112 g. of ferrous sulfate in 2.0 ml of distilled water was added dropwise. After 5 minutes, 0.4533 g. of 30% hydrogen peroxide was added dropwise. After one hour, 0.1133 g. of 30% hydrogen peroxide was added dropwise. The reaction mixture was then stirred under nitrogen bubbling for 3 hours. The reaction product was de-watered by adding 50 g. of acetone and allowed to stand overnight. The reaction product was then separated from the reaction medium by filtration, tray dried overnight in a 45° C. oven and finally vacuum dried to constant weight at room temperature. It was recovered in the form of beige, free-flowing powder after grinding and screening a 40-mesh sieve. The yield was 90.2%. A 2% solution of this product in water is clear and has a pH of 7.3 and a Brookfield viscosity of 1700 cps at 25° C.

Testing of this product, according to the test method of Example 14, showed no substantive red color on the hair. Wet comb results based on test method of Example 15 were rated 4, 8, 5 for the hair tress dipping in water, dipping in 1% polymer solution and rinsing in water, respectively, and were inferior to the wet comb results of Polymers 1–12 of this invention.

EXAMPLE 17

This example demonstrates that the cationic cellulose polymers of the present invention are compatible with a number of typical anionic and amphoteric surfactants for formulating conditioning shampoos, conditioning mousses and creme rinse conditioners.

| CONDITIONING SHAMPOO A typical conditioning shampoo formulation was prepared using the following ingredients: | |
|---|---|
| Ingredient | Weight, g. |
| Distilled water | 37.6 |
| Hydroxypropyl methylcellulose (Methocel ® E4M, Dow) | 0.3 |
| MEPDAC—HEC polymer (polymer 8) | 1.0 |
| Ethanol SDA-40 | 5.0 |
| Citric Acid | 0.5 |
| Ethylenediaminetetraacetic acid (EDTA, Cheelox ® BF-13, GAF) | 0.1 |
| Triethanolamine lauryl sulfate (Standapol ® T, Henkel) | 40.0 |
| Sodium lauryl sulfate (Standapol ® WAG, Henkel) | 10.0 |
| Coconut oil diethanolamine condensate (GAFAMIDE ® CDD-518, GAF) | 5.0 |
| Kathon ® CG microbicide* (Rohm & Haas) | 0.5 |
| | 100.0 |

*1.5% 5-chloro-2-methyl-4-isothiazolin-3-one (active) in 98.5% of 2-methyl-4-isothiazolin-3-one (inert)

The cationic cellulose polymer, Polymer 8, was dissolved completely in ⅔ of the distilled water by mixing at 25° C. and Methocel ® E4M was dissolved completely in the remaining ⅓ of the distilled water at 85° C. After blending these two solutions completely, the remaining ingredients were added in the order listed to form a conditioning shampoo. When treated on the hair, it results in combing wet hair easily and hair styles with luster appearance, cleaner feel, better curl retention and manageability.

| CONDITIONING MOUSSE A typical aerosol conditioning mousse was prepared using the following ingredients: | |
|---|---|
| Ingredient | Weight, g. |
| Distilled water | 68.0 |
| MEPDAC-HEC Polymer (Polymer 1) | 1.5 |
| Ethanol SDA-40 | 15.0 |
| Polyoxyethylated (2) oleyl alcohol (Emulphor ® ON-870, GAF) | 0.5 |
| Propellant A-46 (20/80 propane/isobutane blend) | 15.0 |
| | 100.0 |

The cationic cellulose polymer, Polymer 8, was dissolved completely in the distilled water by mixing at 25° C. After adding ethanol and Emulphor ® ON-870, the polymer solution was charged with Propellant A-46 in a aerosol bottle with a Mousse Valve (Precision Valve Corp.). The aerosol can delivered a stable foam after it was well shaken. When treated on the hair, it results in combing wet hair easily and hair styles with luster appearance, cleaner feel and better curl retention and manageability.

CREME RINSE CONDITIONER
A typical creme rinse conditioner was prepared using the following ingredients:

| Ingredient | Weight, % |
| --- | --- |
| Distilled water | 90.7 |
| MEPDAC—HEC Polymer (Polymer 1) | 2.0 |
| Cetyl Alcohol | 2.0 |
| Stearyl Alcohol and Ceteareth-20 (Amerchol) | 3.0 |
| Tocopherol Acetate (Henkel) | 0.3 |
| Jojoba Oil (Lipo Chemicals) | 0.5 |
| Glyceryl stearate | 1.0 |
| Propylene Glycol, Diazolidinyl urea, | 0.5 |
| Methylparaben & propylparaben (Sutton Labs.) | |
| | 100.0 |

The cationic cellulose polymer, Polymer 1, was dissolved completely in the distilled water by mixing at 25° C. The remaining ingredients were added in the order listed and mixed thoroughly to form a creme rinse conditioner. When treated on the hair, it results in an improvement in wet combability and hair styles with luster appearance, cleaner feel and better curl retention.

What is claimed is:

1. A copolymer of a cellulose containing a hydroxy group on which is grafted, by replacement of the hydrogen atom of the hydroxy group, a quaternized amino lactam having the formula

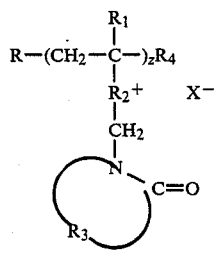

wherein $R_1$ is hydrogen or methyl; $R_2$ is a quaternized $C_4$ to $C_{29}$ moiety of an amino amide, an amino ester or a cyclic amine having 1 to 2 nitrogen atoms in a 5 to 6 membered N-heterocyclic ring, which ring is optionally substituted with lower alkyl; $R_3$ is $C_3$ to $C_8$ alkylene optionally substituted with lower alkyl; $R_4$ is hydrogen or hydroxy and z is an integer having a value of from 1 to 1000.

2. A cellulosic graft polymer containing units

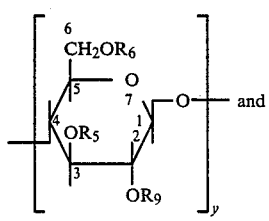

(b) units of (a) wherein at least one hydrogen of $R_5$, $R_6$ and $R_9$ is replaced by a quaternized amino lactam having the structure

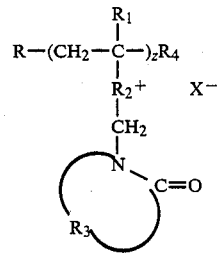

wherein $R_1$ is hydrogen or methyl; $R_2$ is a quaternized $C_4$ to $C_{29}$ moiety of an amino amide, an amino ester or a cyclic amine having 1 to 2 nitrogen atoms in a 5 to 6 membered N-heterocyclic ring, which ring is optionally substituted with lower alkyl; $R_3$ is $C_3$ to $C_8$ alkylene optionally substituted with lower alkyl; $R_4$ is hydrogen or hydroxy; $R_5$, $R_6$ and $R_9$ are each hydrogen, hydroxy, lower alkyl, lower hydroxyalkyl, lower alkyloxyalkyl carboxymethyl or carboxymethyl lower hydroxyalkyl; X is a halide anion and z is an integer having a value of from 1 to 1000.

3. The copolymer of claim 2 which is composed of from about 50 mole % to about 99 mole % of component (a).

4. The copolymer of claim 3 which is composed of from 75 mole % to 98 mole % of component (a).

5. The copolymer of claim 4 which contains at least 85 mole % of component (a).

6. The copolymer of claim 2 having from 50 to 20,000 units of (a) and (b).

7. The copolymer of claim 6 having from 200 to 8,000 units of (a) and (b).

8. The copolymer of claim 2 wherein only one hydrogen of $R_5$, $R_6$ and $R_9$ is quaternized with said quaternized amino lactam in component (b).

9. The copolymer of claim 2 wherein $R_2^+$ of component (b) has the structure

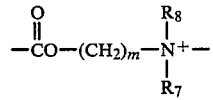

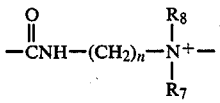

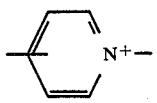

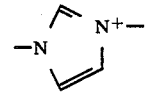

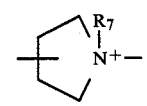

wherein m and n each have a value of from 1 to 20 and $R_7$ and $R_8$ are each lower alkyl.

10. The copolymer of claim 9 wherein $R_7$ and $R_8$ are both methyl.

11. The copolymer of claim 9 wherein the quaternized amino lactam is 2-methacryloyloxyethyl[(1-pyrrolidonyl)methyl]dimethyl ammonium chloride.

12. The copolymer of claim 9 wherein the quaternized amino lactam is 3-[(1-pyrrolidonyl)methyl]1-vinylimidazolium chloride.

13. The copolymer of claim 9 wherein the quaternized amino lactam is 1-[(1-pyrrolidonyl)methyl]-4-vinylpyridinium chloride.

14. The copolymer of claim 9 wherein the quaternized amino lactam is 3-methacrylamidopropyl[(1-pyrrolidonyl)methyl]dimethyl ammonium chloride.

15. The process which comprises contacting a keratinous substrate with a conditioning amount of the copolymer of claim 1.

16. The process which comprises adding an effective conditioning amount of the copolymer of claim 1 to a cosmetic formulation.

17. The process of claim 16 wherein said cosmetic formulation is a hair or skin treatment formulation.

18. The process of claim 16 wherein between about 0.01% and about 10% by weight of the copolymer of claim 1 is added to said cosmetic formulation.

19. The process of claim 17 wherein between about 0.2% and about 3% by weight of the copolymer of claim 1 is added.

20. The process of claim 16 wherein said formulation is a shampoo and wherein the copolymer of claim 1 is less than 20% quaternized.

21. The process which comprises adding an effective dye fixing amount of the copolymer of claim 1 to a hair dying formulation.

22. The process of adding an effective conditioning or dye fixing amount of the copolymer of claim 1 to a fur or pelt processing formulation.

23. A shampoo containing between about 0.2% and about 3% by weight of the copolymer of claim 5.

24. A skin cleansing formulation containing between about 0.01% and about 10% by weight of the copolymer of claim 1.

25. A permanent wave reducing solution containing from about 0.2% and about 3% by weight of the copolymer of claim 1.

* * * * *